(12) United States Patent
Worsoee (10) Patent No.: US 7,850,668 B2
(45) Date of Patent: Dec. 14, 2010

(54) OSTOMY APPLIANCE

(75) Inventor: Bjarne Worsoee, Tikoeb (DK)

(73) Assignee: Coloplast A/S, Humlebaek (DK)

( * ) Notice: Subject to any disclaimer, the term of this patent is extended or adjusted under 35 U.S.C. 154(b) by 620 days.

(21) Appl. No.: 11/579,407

(22) PCT Filed: May 3, 2005

(86) PCT No.: PCT/EP2005/052022

§ 371 (c)(1),
(2), (4) Date: Nov. 2, 2006

(87) PCT Pub. No.: WO2005/105007

PCT Pub. Date: Nov. 10, 2005

(65) Prior Publication Data

US 2007/0270772 A1    Nov. 22, 2007

(30) Foreign Application Priority Data

May 3, 2004    (DK) .............................. 2004 00697

(51) Int. Cl.
*A61F 5/44* (2006.01)
(52) U.S. Cl. .................. 604/333; 604/317; 604/323; 604/324; 604/326; 604/327; 604/331; 604/332; 604/337; 604/338; 604/339; 604/341; 604/350; 604/355
(58) Field of Classification Search ......... 604/331–333, 604/337–339
See application file for complete search history.

(56) References Cited

U.S. PATENT DOCUMENTS

| | | | |
|---|---|---|---|
| 4,366,836 A | | 1/1983 | Villari |
| 4,490,145 A | * | 12/1984 | Campbell .................. 604/333 |
| 4,938,750 A | | 7/1990 | Leise, Jr. |
| 5,401,264 A | | 3/1995 | Leise, Jr. |
| 5,667,502 A | | 9/1997 | Holtermann |
| 5,690,622 A | * | 11/1997 | Smith et al. .................. 604/333 |
| 6,517,429 B1 | * | 2/2003 | O'Connell et al. ............ 454/56 |

(Continued)

FOREIGN PATENT DOCUMENTS

EP    0 850 613 A1    7/1998

(Continued)

OTHER PUBLICATIONS

Office Action, JP.

*Primary Examiner*—Tatyana Zalukaeva
*Assistant Examiner*—Ilya Y Treyger
(74) *Attorney, Agent, or Firm*—Coloplast Corp., Coloplast A/S; Daniel G. Chapik; Nicholas R. Baumann (57) ABSTRACT

A collecting bag for an ostomy appliance, said collecting bag having a front wall and a rear wall, the rear wall having an opening through which waste material may enter the collecting bag, and wherein a manipulation pocket is defined in the front and/or the rear wall of the collecting bag, said manipulation pocket extending into the collecting bag and comprising transfer means adapted to sealed transfer of mechanical movement from the surroundings to the interior of the collecting bag. The sealed transfer of movement can be used to open a passage inside the collecting bag such that flatus gasses may pass through a deodorizing filter, which prior to opening of the passage is protected such that it is not contaminated.

16 Claims, 10 Drawing Sheets

U.S. PATENT DOCUMENTS 6,695,826 B2 * 2/2004 Villefrance .................. 604/333
2003/0236509 A1 12/2003 Silvestrini

FOREIGN PATENT DOCUMENTS

| | | |
|---|---|---|
| EP | 1013249 | 6/2000 |
| EP | 1 101 462 A1 | 5/2001 |
| GB | 2 270 265 A | 3/1994 |
| GB | 2344999 A | 6/2000 |

* cited by examiner

OSTOMY APPLIANCE

This is a nationalization of PCT/EP05/052022 filed May 3, 2005 and published in English.

FIELD OF THE INVENTION

The present invention relates to a collecting bag for an ostomy appliance, the bag comprising an arrangement for sealed transfer of mechanical movement from the surroundings of the bag to the interior of the bag. In particular the present invention relates to a collecting bag comprising a passage inside the bag which may be opened and closed upon sealed transfer of movement from the surrounding of the bag to the interior of the bag.

BACKGROUND OF THE INVENTION

One problem in connection with ostomy appliances is that the discharge of flatus, measured in volume, may exceed the discharge of solid and liquid fecal matter by many hundred percent and therefore there is usually the need for continuous or frequent venting of the intestine or the collecting bag. Normally the outflowing flatus is deodorised with a suitable filter.

However one problem in connection with filters is that the filter may be blocked due to the waste material i.e. the solid and liquid fecal matter. Efforts have been made to overcome the problem and systems wherein the filter may be changed manually by the user have been designed.

One example may be found in U.S. Pat. No. 4,938,750 which describes an ostomy collection pouch comprising a pouch wall which has a plurality of vent passages each containing a filter. Each filter can be exposed in turn simply by moving an adhesive cover from one location to the. The adhesive cover is provided on the outside such that it is possible for the user to access and move the adhesive cover. Thus, as the surface of the filter facing the interior of the pouch is not covered prior to use, a filter may be blocked from the inside before the filter has even been used.

Accordingly, it is desired to provide an ostomy appliance with a filter having an inner surface facing the interior of the bag and an outer surface facing the exterior of the bag and wherein the inner surface is protected from contamination prior to use of the filter.

Furthermore, it is desired to provide a solution wherein it is avoided that the ostomy appliance must be opened in order to remove a cover protecting an unused filter. Accordingly, it is an object of the present invention to achieve sealed transfer of movement from the surroundings of the appliance to the interior of the appliance.

An example of transfer of movement from the surroundings to the interior of the appliance is seen in EP 0 850 613 which describes a body waste receiving pouch comprising a deodorant-containing body which is nipped by fingers from the outside to apply pressure to the deodorant-containing body, whereby the deodorant-containing body is broken to discharge a deodorant from within the pouch member. However as the deodorant-containing body is provided behind a smooth surface it may be difficult to get grip of or nip the body. Furthermore, as the body must be nipped there exist a risk of tearing a hole in the pouch whereby gasses and waste material may exit the pouch.

It is an object of the present invention to overcome the above mentioned problems.

DESCRIPTION OF THE INVENTION

The present invention relates to a collecting bag for an ostomy appliance, said collecting bag having a front wall and a rear wall, the rear wall having an opening through which waste material may enter the collecting bag, and wherein a manipulation pocket is defined in the front and/or the rear wall of the collecting bag, said manipulation pocket extending into the collecting bag and comprising transfer means adapted to sealed transfer of mechanical movement from the surroundings to the interior of the collecting bag.

The manipulation means may extend through a wall of the manipulation pocket and comprise an interior part and an exterior part, the interior part extending from the manipulation pocket into the collecting bag and the exterior part extending from the manipulation pocket to the exterior of the collecting bag so as to be accessible to the user.

By gripping the transfer means the user may manipulate the interior of the collecting bag, whereby it will be possible e.g. to remove a cover protecting a flatus filter from contamination. As the movement is performed under sealed conditions, no flatus gasses bypass the filter and unpleasant situations are avoided.

The manipulation pocket provides the movability of the transfer means without interfering with the general shape of the pouch and ensures that manipulation does not stress the material of the front wall or the rear wall. It is avoided that finger nails of a user tear a hole in the collecting bag as it is not necessary to nip through a wall of the bag. The length of the manipulation pocket determines how much the transfer means may be moved inside the bag.

The transfer means may be provided as a long rigid element e.g. rod-like plastic element. One advantage of a rod-like element is that it makes it possible to transfer movement in both an inward direction and an outward direction. Alternatively the transfer means may be provided as a string e.g. of the same kind of flexible sheet material (or a similar kind of material) as the front wall or the rear wall of the collecting bag. A transfer means in the form of a string could alternatively be made of a cotton string or a nylon string or any other kind of string.

A bottom part of the transfer means may be attached to the bottom of the manipulation pocket and extend out of the pocket, whereby an opposite top part of the transfer means can be gripped by the user. The transfer means may be glued or welded to the pocket or attached by another attachment method known per se.

The top part of the transfer means can initially be releasably attached to the front or rear wall e.g. by means of a sticker.

The transfer means may be provided with indicating colours such that it is possible for the user to see whether the transfer means has been pulled or not and thereby whether a passage is open in the collecting bag or not.

In one embodiment the length of the manipulation pocket is at least twice the width of the manipulation pocket. Alternatively the length is three times the width or four time the width or at least five times the width. The width of the manipulation pocket may be less than 10 mm such as less than 5 mm.

The hole in the front and/or rear wall into the manipulation pocket may be designed such a raising pressure e.g. due to flatus gasses in the collecting bag cannot force the manipulation pocket to extend out of the collecting bag. In one embodiment this is achieved by providing the hole in the front and/or rear wall in an elongated and narrow shape. E.g. such that the gap between the rim of the hole and the transfer means at no point is greater than 0.2 mm.

The manipulation pocket may be made of a material with memory i.e. which has a tendency to move towards a predetermined position. In one embodiment the manipulation pocket has a tendency to extend into the bag and away from a position wherein the manipulation pocket creases.

In one embodiment the manipulation bag is defined in the front wall or in the rear wall. Another embodiment provides a manipulation pocket defined between the front and rear wall of the collecting bag. In the latter embodiment the manipulation pocket is defined in a seam between the front and rear wall. A part of the rim of the front and rear wall may be left unassembled in order to provide the hole for placing the manipulation pocket. The parts of the front and rear wall which are unconnected may then each be connected with a wall of the manipulation pocket such that flatus gasses may not escape the collecting bag through the hole.

In a further embodiment the manipulation pocket is adapted to be changed between a closing position wherein a passage in the collecting bag is closed and an opening position wherein the passage is open. Alternatively, the movement from the closing position to the opening position is irreversible e.g. in the case where the transfer means can only exert pulling forces.

When the manipulation pocket is in the dosing position, a side wall (or an extension) of the manipulation pocket is adapted to cover the passage. In the closing position the sealing of the passage may be improved by attaching a part of the wall to the edge of the passage by an adhesive which in an embodiment is releasable or resealable.

The passage can be adapted to allow intestinal gasses to pass from the interior of the collecting bag to the surroundings of the collecting bag, when the manipulation pocket is in the opening position. A deodorizing filter may be provided in the passage. Furthermore, a pre-filter may be provided in the passage. The prefilter can be adapted to prevent waste material from contaminating the deodorizing filter. A membrane may be provided which prevents waste material from escaping the collecting bag. The order of the elements in the passage seen from the inside of the collecting bag may be pre-filter, deodorizing filter and membrane. However the elements may be placed in any sequence.

In an alternative embodiment the collecting bag may be provided with a first chamber and a second chamber. Initially the waste material may only enter the first chamber, while the second chamber is closed. A passage may be provided between the first chamber of the collecting bag and the second chamber of the collecting bag. Thus, when the first chamber is nearly filled up the user may open the passage between the first chamber and the second chamber and thus there is room for more waste material.

In one embodiment two sheets of flexible material define a first wall and a second wall of the manipulation pocket and the first and second walls are sealingly attached to each other along a first part of an edge of each of the walls. Either the first or the second wall of the manipulation pocket can be used to block the passage when the manipulation pocket is in the closing position.

The edge of the first wall and the second wall of the manipulation pocket can be divided into a first part and a second part. In one embodiment the first wall and the second wall of the manipulation pocket are attached to each other along their respective first parts. At the same time the second part of the first wall of the manipulation pocket is attached to the rim of the front wall of the collecting bag and the second part of the second wall of the manipulation pocket is attached to the rim of the rear wall of the collecting bag.

DETAILED DESCRIPTION OF THE INVENTION

An embodiment of the invention will now be described in details with reference to the drawings in which.

BEST MODE OF CARRYING OUT THE INVENTION

The invention is now explained more in detail with reference to the drawings showing preferred embodiments of the invention.

Figure 1A:
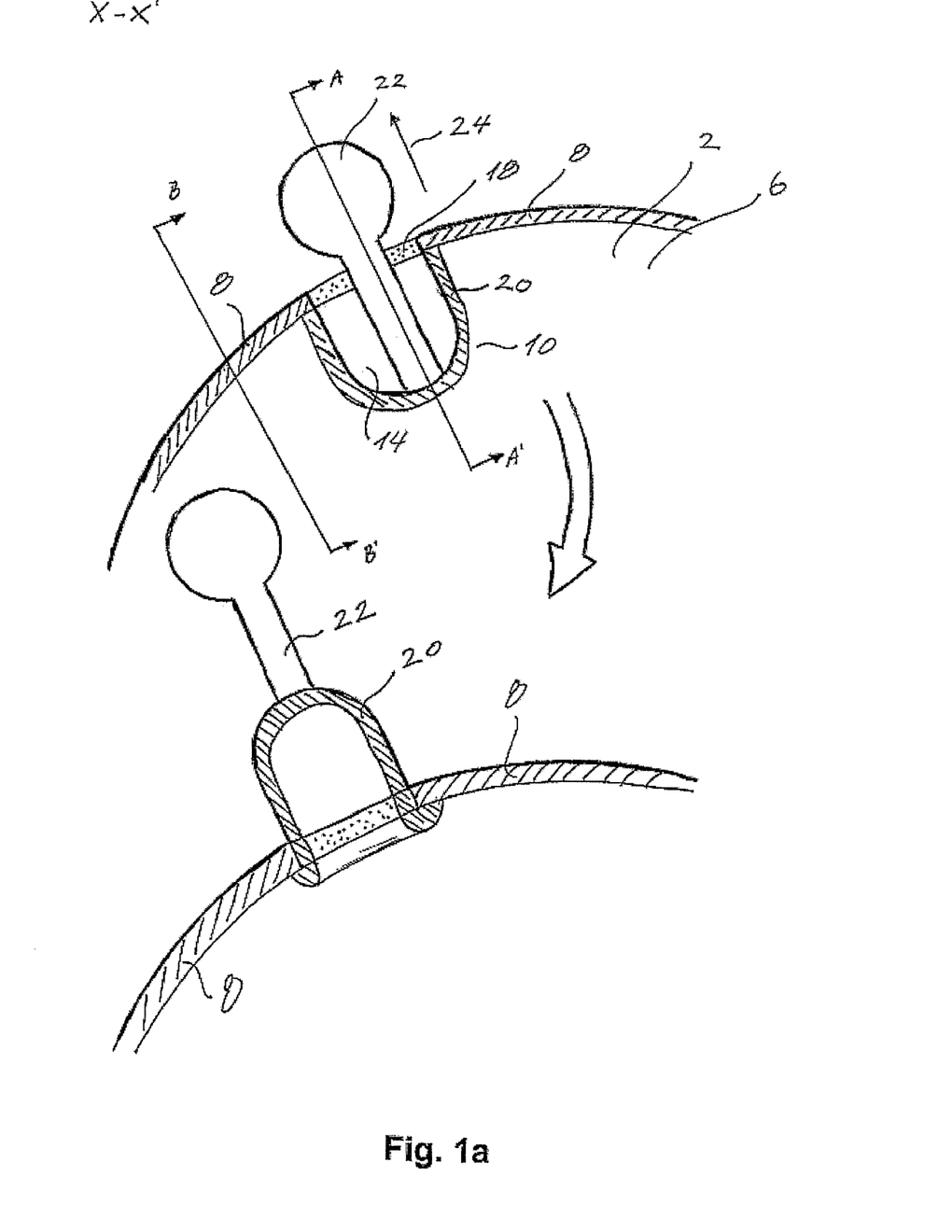
FIGS. 1a and 1b show a front view and a sectional view of the general principle of the present invention.
Figure 1B:
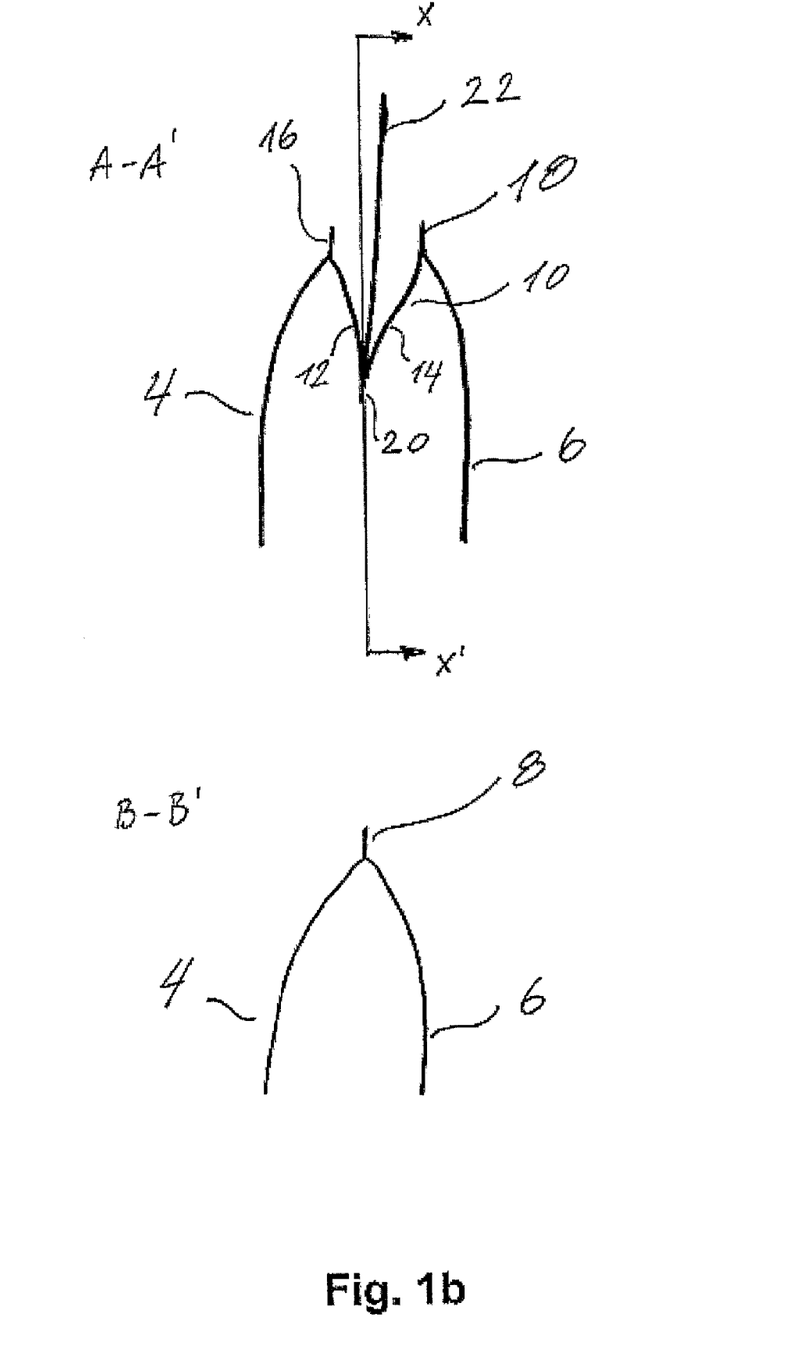

FIGS. 1a and 1b disclose the general principle underlying the present invention. A part of an ostomy appliance 2 is shown. The ostomy appliance 2 comprises a front wall 4 and a rear wall 6 which are connected by a first seam 8. A manipulation pocket 10 comprises a first wall 12 and a second wall 14. The first wall 12 is seamed to the front wall 4 in a second seam 16 and the second wall 14 is seamed to the rear wall 6 in a third seam 18. The first wall 12 and the second wall 14 are seamed together in a fourth seam 20. A transfer means 22 is attached to a bottom part of the manipulation pocket 10. The transfer means is connected to the fourth seam 20. As indicated by arrow 24 the transfer means 22 may be used to move the manipulation pocket from a position wherein it extends into the ostomy appliance 2 as shown in the upper part of FIG. 1a to a position wherein it extends out of the ostomy appliance as shown in the lower part of FIG. 1a.

Figure 2A:
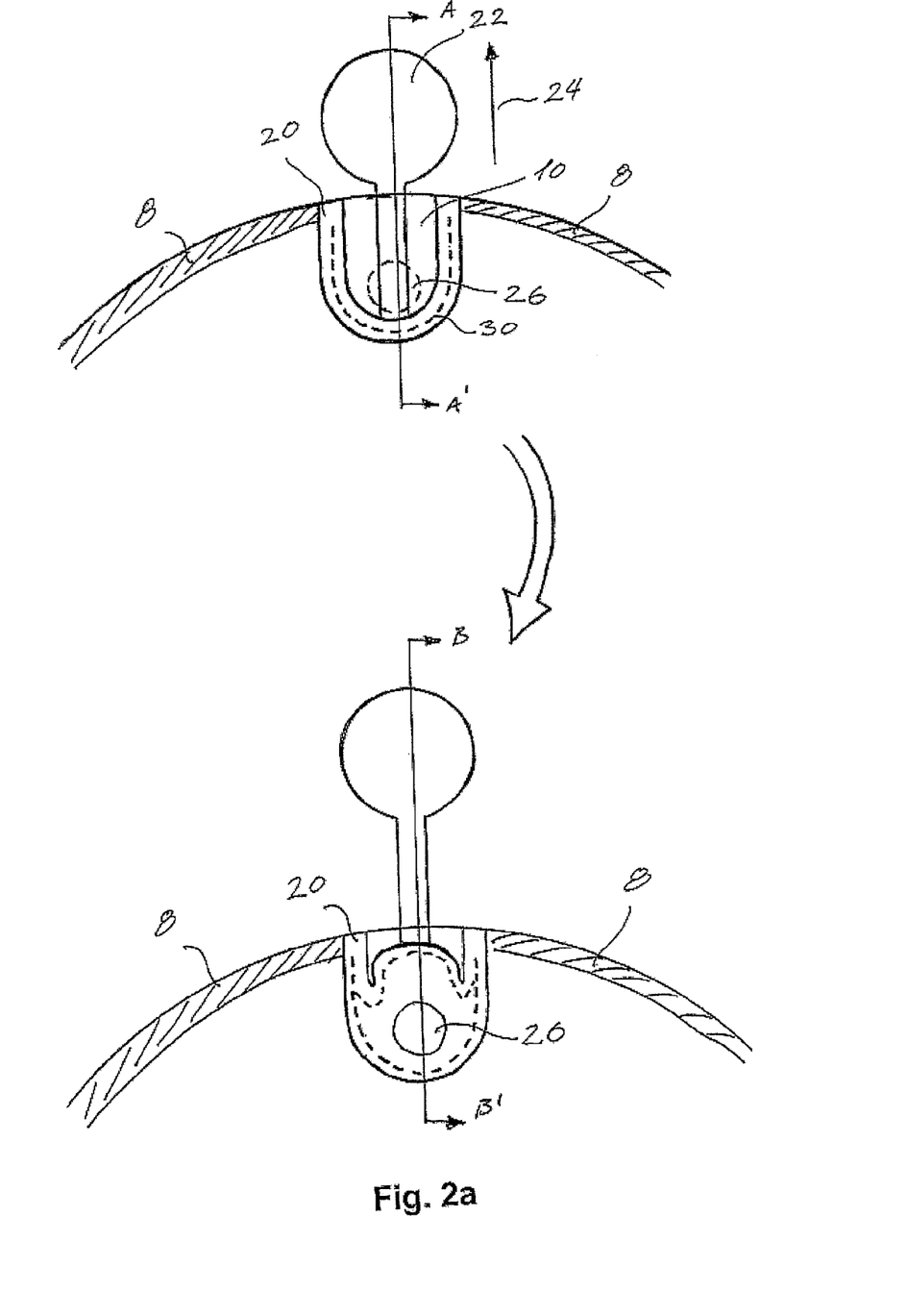
FIGS. 2a and 2b show a front view and a sectional view of a pocket covering a passage into a filter.
Figure 2B:
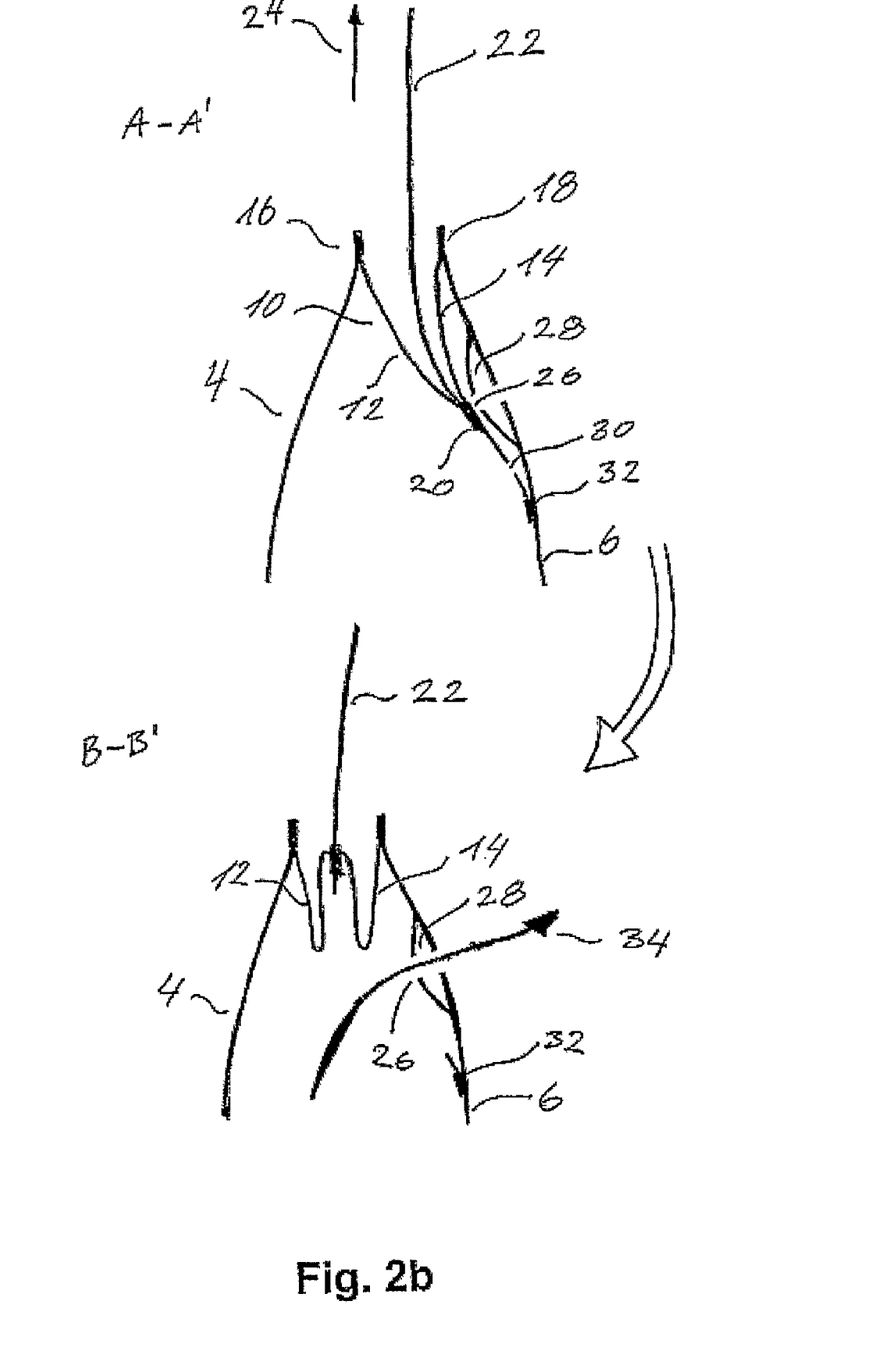

The embodiment of FIGS. 2a and 2b is based on the principle of FIGS. 1a and 1b. However in FIGS. 2a and 2b the manipulation pocket is used to cover a passage 26 into a filter 28. The manipulation pocket comprises a perforated line 30 (the upper part of FIG. 2b is a sectional view of the upper part of FIG. 2a and in the sectional view the section has been made through one of the holes in the perforated line). A part of the fourth seam 20 has been attached to the rear wall 6 in an attachment point 32. When the transfer means 22 is pulled the perforated line is broken and flatus gasses may pass through the filter 28 as indicated by arrow 34.

Figure 3:
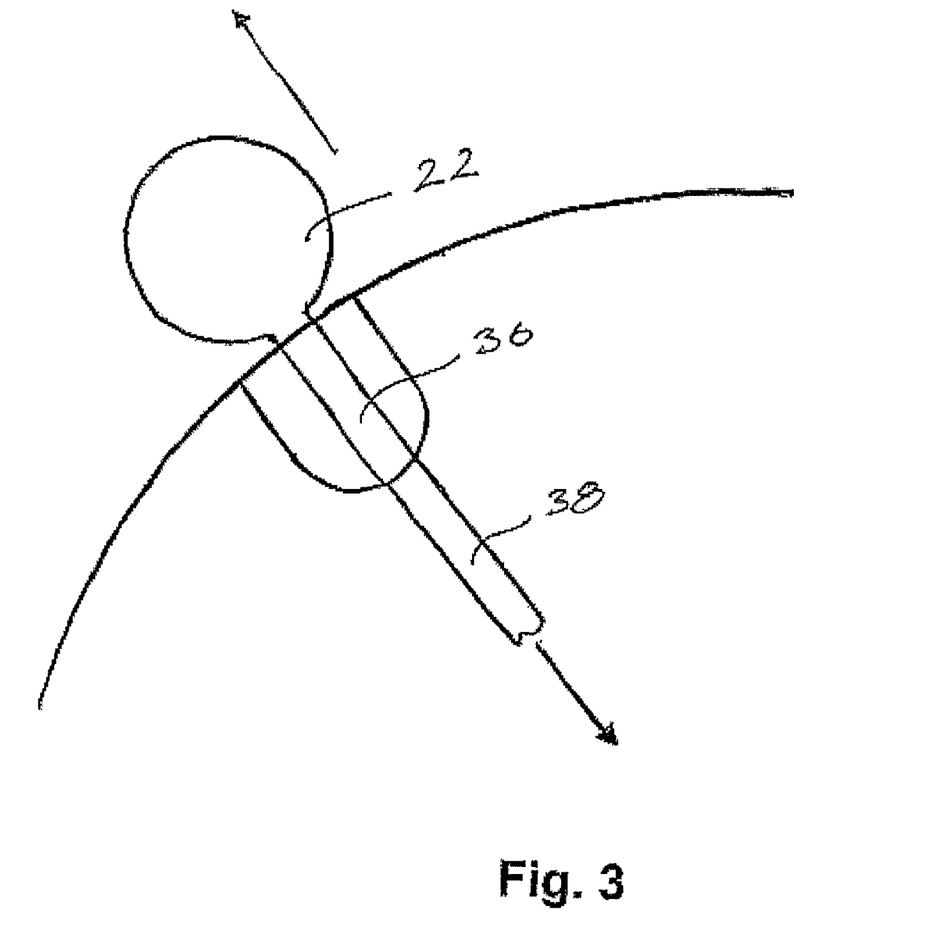
FIGS. 3 and 4 show a transfer means according to the present invention.
Figure 4:
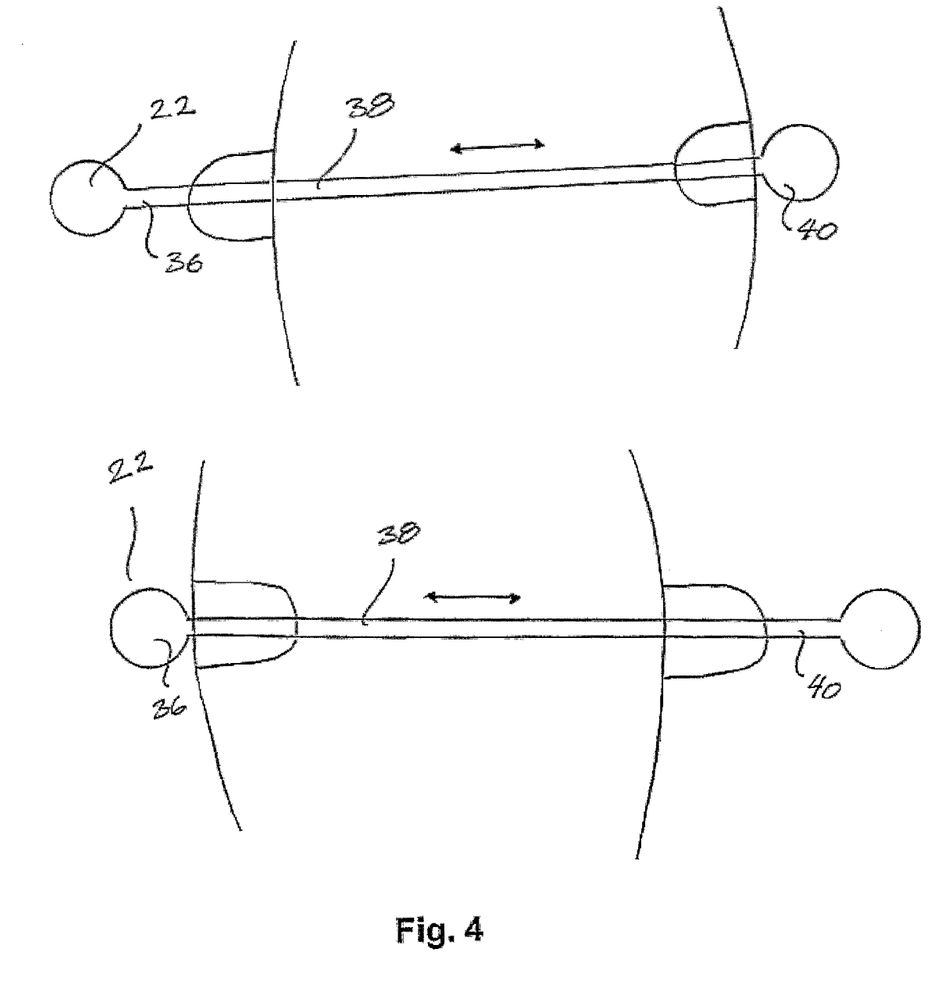

In FIG. 3 the transfer means 22 comprises a first part 36 and a second part 38. The first part 36 is provided on the outer side of the ostomy appliance while the second part 38 is provided on the inner side. In FIG. 4 a further third part 40 of the transfer means 22 is provided. In both figs. the transfer means may be used for sealed transfer of movement from the outside to the inside of the ostomy appliance.

Figure 5:
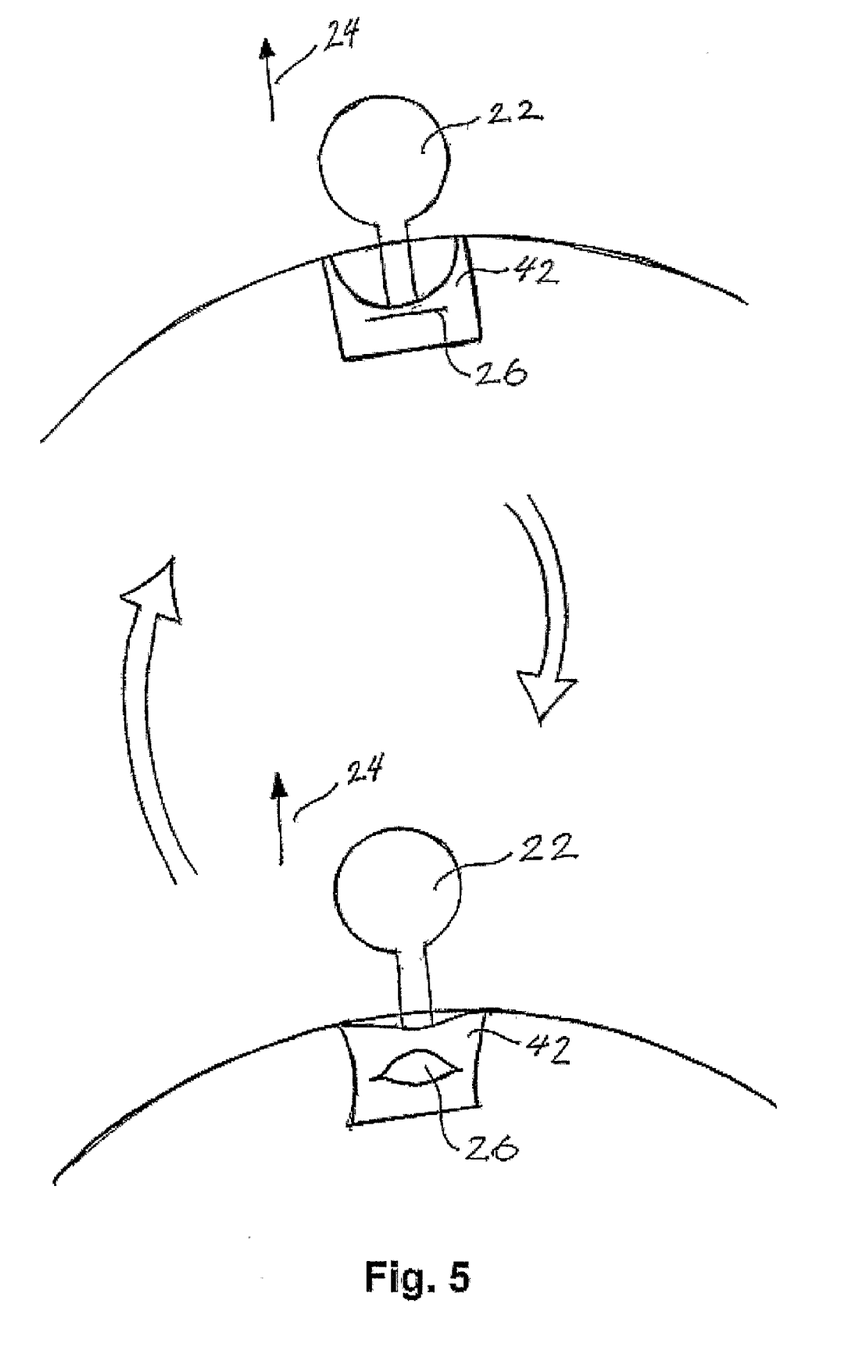
FIG. 5 shows an opening into a filter, which may be controlled by a transfer means.

In FIG. 5 a passage 26 is provided in an element 42 which is designed to close the passage when no force is applied to the transfer means 22 in the direction indicated by arrow 24.

Figure 6:
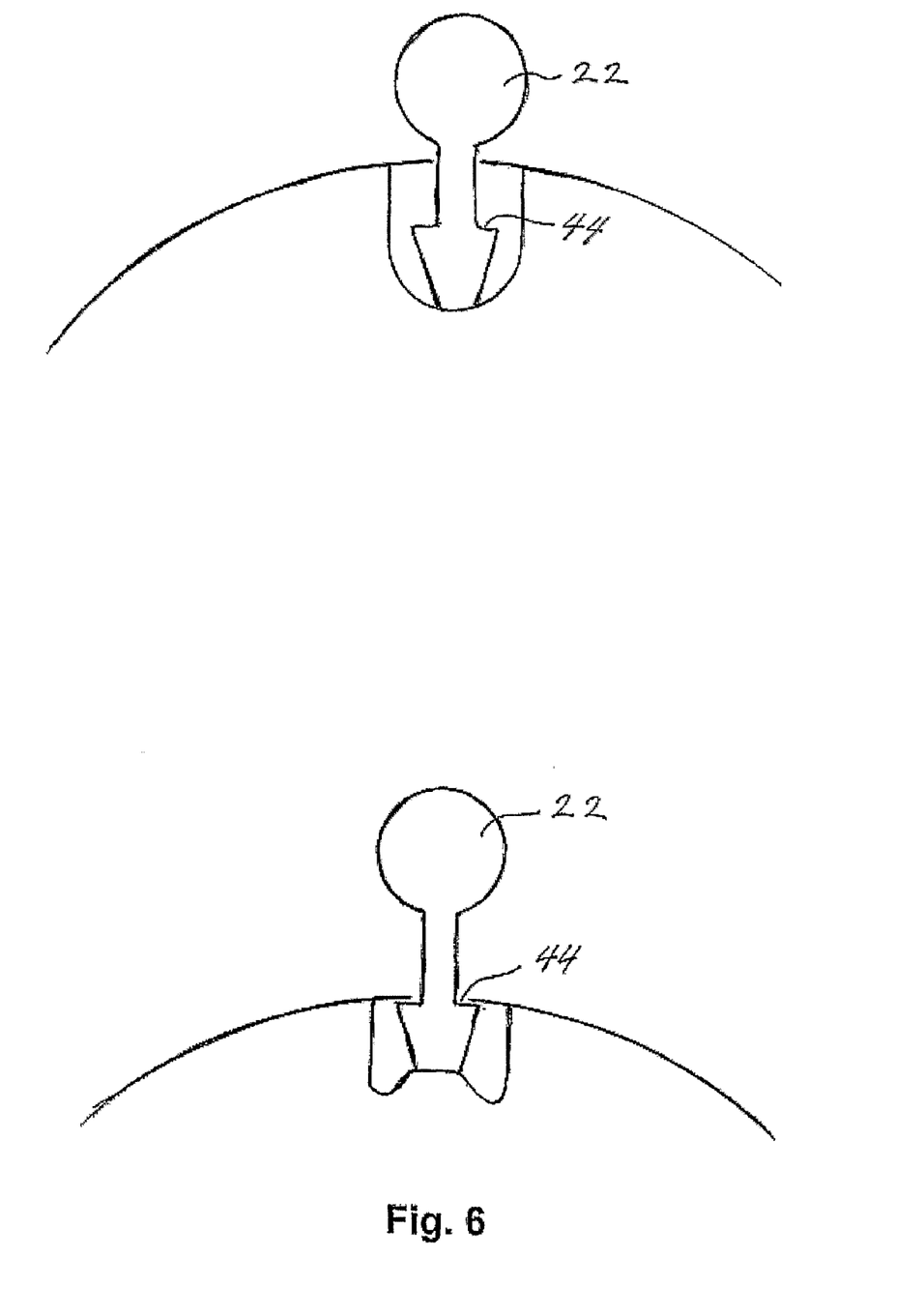
FIGS. 6-8 show different embodiments of means for limiting the distance the transfer means can be moved.
Figure 7:
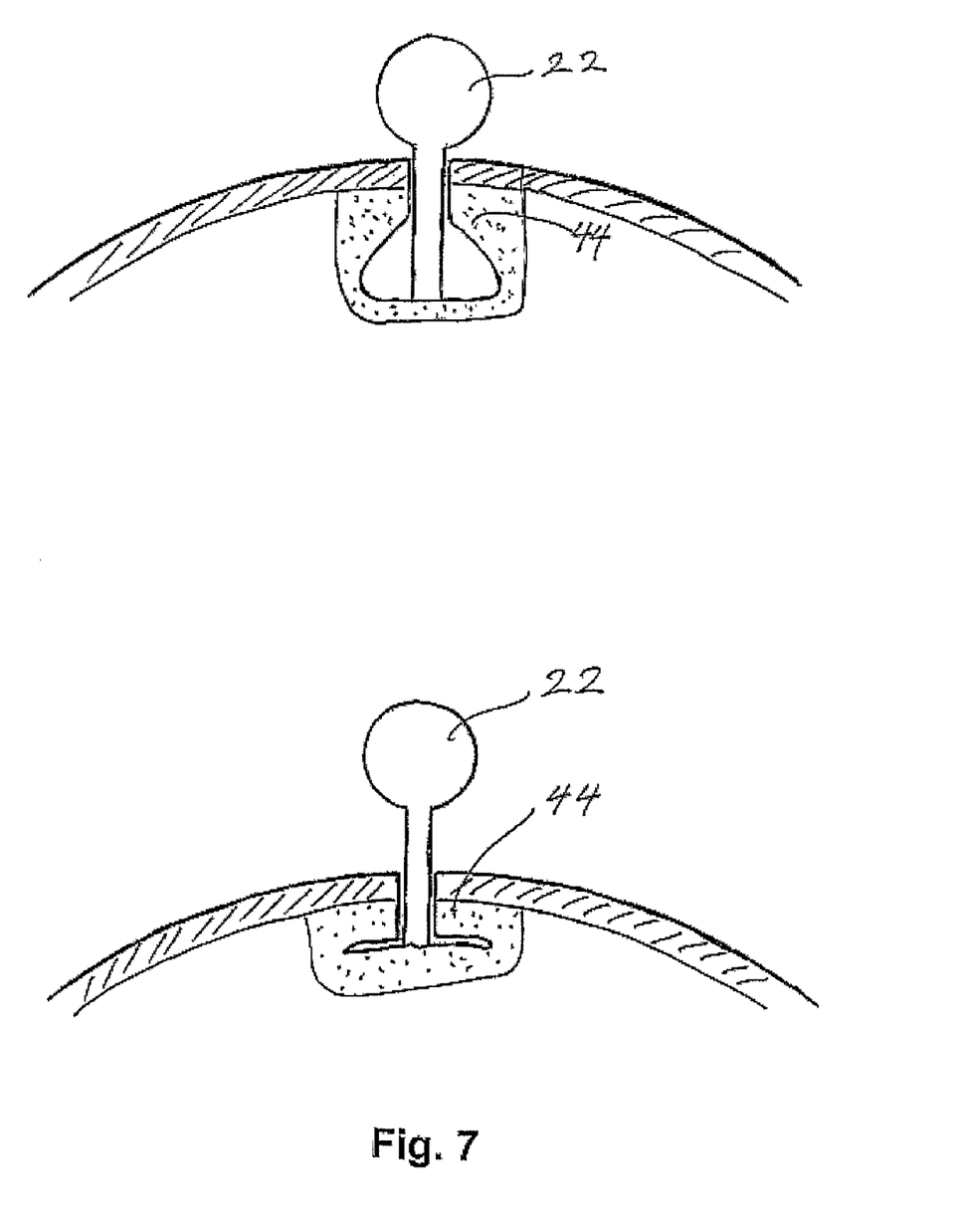
Figure 8:
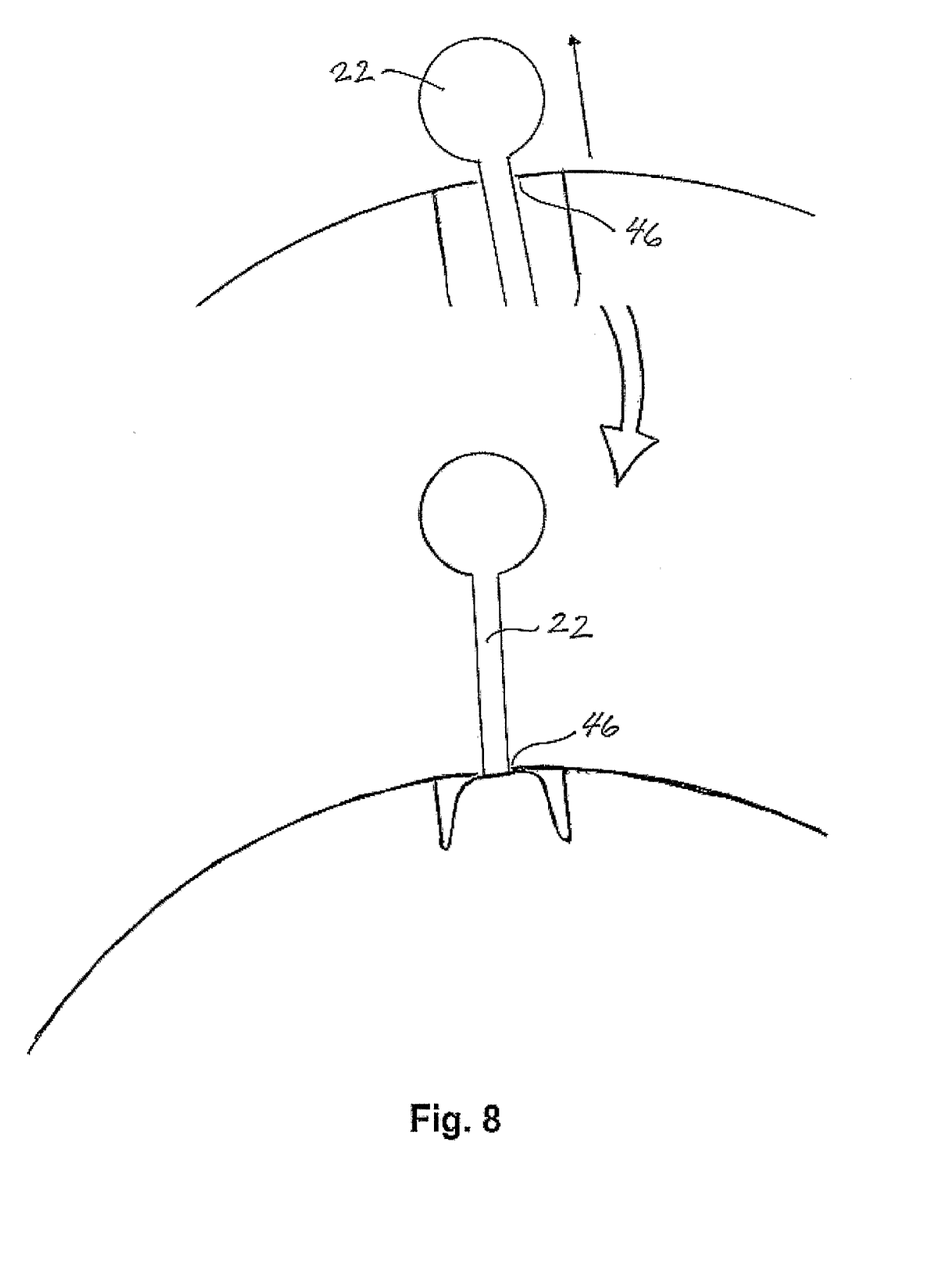

FIGS. 6-8 show different embodiments wherein the appliance is designed so as to comprise movement limiting means 44 which limit the distance the transfer means 22 may be moved. In FIG. 6 the movement limiting means 44 is a portion of the transfer means 22 which has a diameter greater than the rest of the transfer means 22. In FIG. 7 the seam between the first wall and the second wall of the manipulation pocket is designed to limit the movement. In FIG. 8 the seam between the front and the rear wall is designed such that only the transfer means may be moved out the hole 46 but the manipulation bag may not be pulled out of the hole.

The invention claimed is:

1. A collecting bag for an ostomy appliance, said collecting bag comprising:
a front wall and a rear wall, the rear wall having an opening through which waste material enters the collecting bag, a manipulation pocket provided in the collecting bag, said manipulation pocket extending into the collecting bag and so configured to prevent accumulation of the waste material on a filter element of the collecting bag, and a transfer element disposed in the manipulation pocket, the transfer element having a first portion attached to the manipulation pocket and a second portion that projects out from the manipulation pocket and available to a user of the ostomy appliance to move the manipulation pocket away from the filter element to enable flatus gasses to exit the collecting bag.

2. An ostomy appliance according to claim 1, wherein the length of the manipulation pocket is at least twice the width of the manipulation pocket.

3. An ostomy appliance according to claim 1, wherein the manipulation pocket is defined between the front and rear wall of the collecting bag.

4. An ostomy appliance according to claim 1, wherein the manipulation pocket is adapted to be changed between a closing position wherein a passage in the collecting bag is closed and a opening position wherein the passage is open.

5. An ostomy appliance according to claim 4, wherein a wall of the manipulation pocket is adapted to cover the passage when the manipulation pocket is in the closing position.

6. An ostomy appliance according to claim 4, wherein the passage is adapted to allow intestinal gasses to pass from an interior of the collecting bag to an exterior of the collecting bag when the manipulation pocket is in the opening position.

7. An ostomy appliance according to claim 4, wherein a deodorizing filter is provided in the passage.

8. An ostomy appliance according to claim 4, wherein the passage is provided between a first chamber of the collecting bag and a second chamber of the collecting bag.

9. An ostomy appliance according to claim 1, wherein two sheets of flexible material define a first wall and a second wall of the manipulation pocket and wherein the first and second walls are sealingly attached to each other along a first part of an edge of each of the walls.

10. An ostomy appliance according to claim 9, wherein a second part of each of the first and second walls respectively are sealingly attached to the front and/or rear wall of the collecting bag.

11. An ostomy appliance according to claim 1, wherein the transfer element comprises a portion that extends inside to an interior of the collecting bag.

12. An ostomy appliance according to claim 1, wherein the transfer element comprises a shaft that extends out of the manipulation pocket, the shaft comprising the first portion coupled to a bottom of the manipulation pocket, with the first portion having a base diameter that is larger than a diameter of the shaft, the base diameter sized to limit a distance that the manipulation pocket moves out of the collecting bag.

13. A collecting bag for an ostomy appliance, the collecting bag comprising:
a front wall sealed to a rear wall to define a collection volume, one of the front wall and the rear wall defining an opening for the transfer of waste material into the collection volume;
a filter sealed to the opening formed in the one of the front wall and the rear wall of the collecting bag, the filter comprising an inner surface facing the collection volume and an outer surface facing exterior to the collecting bag;
a manipulation pocket sealed between the front and rear walls of the collecting bag;
a transfer mechanism coupled to the manipulation pocket;
wherein the manipulation pocket is configured to be moved in a first direction into the collection volume to cover the inner surface of the filter and in a second direction away from the filter to uncover the inner surface of the filter;
wherein the transfer mechanism comprises movement limiting means configured to limit a distance that the manipulation pocket moves in the second direction.

14. The collecting bag of claim 13, wherein the transfer mechanism comprises a rigid member coupled to the manipulation pocket, the rigid member extending out of a hole defined in collecting bag, and the movement limiting means is configured to allow the rigid member to pass through the hole and deny passage of the manipulation pocket through the hole.

15. The collecting bag of claim 13, manipulation pocket is sealed to a seam formed between the front and rear walls of the collecting bag.

16. The collecting bag of claim 13, wherein the collecting bag defines a passage and the manipulation packet is movable to cover the passage and movable to selectively uncover the passage.

* * * * *